(12) United States Patent
Schwieker et al.

(10) Patent No.: US 7,329,224 B2
(45) Date of Patent: Feb. 12, 2008

(54) THERAPY COMBINATION

(75) Inventors: Horst Hartwig Schwieker, Hamburg (DE); Thomas Schnabel, Hamburg (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 420 days.

(21) Appl. No.: 10/520,991

(22) PCT Filed: Jul. 4, 2003

(86) PCT No.: PCT/IB03/02983

§ 371 (c)(1),
(2), (4) Date: Jan. 10, 2005

(87) PCT Pub. No.: WO2004/006786

PCT Pub. Date: Jan. 22, 2004

(65) Prior Publication Data

US 2005/0228263 A1 Oct. 13, 2005

(30) Foreign Application Priority Data

Jul. 10, 2002 (DE) .............................. 102 31 071

(51) Int. Cl.
*A61B 8/00* (2006.01)

(52) U.S. Cl. ...................................... 600/439; 600/408

(58) Field of Classification Search ................ 600/408, 600/439, 101, 117, 427
See application file for complete search history.

(56) References Cited

U.S. PATENT DOCUMENTS

| 5,275,772 | A | 1/1994 | Yamamoto et al. |
| 5,368,032 | A | 11/1994 | Cline et al. |
| 5,836,898 | A * | 11/1998 | Schwieker .................... 601/4 |
| 5,944,663 | A | 8/1999 | Kuth et al. |
| 6,216,029 | B1 * | 4/2001 | Paltieli ...................... 600/427 |
| 6,217,214 | B1 * | 4/2001 | Cabral et al. ............... 378/196 |
| 6,461,314 | B1 * | 10/2002 | Pant et al. ..................... 601/2 |
| 6,990,368 | B2 * | 1/2006 | Simon et al. ............... 600/425 |

FOREIGN PATENT DOCUMENTS

DE  195 12 956 C2  10/1996
DE  102 06 193 C1  7/2003

* cited by examiner

*Primary Examiner*—Eleni Mantis Mercader

(57) ABSTRACT

The invention relates to a therapy combination which consists of a locating unit and a therapy unit which includes a therapy head for focusing energy in a focus, said units being movable relative to one another. In order to determine the relative position, each of said two units is provided with a sub-system of a measuring device. The position of the focus can thus be determined relative to an image produced by the locating unit.

9 Claims, 2 Drawing Sheets

THERAPY COMBINATION

Figure 1:
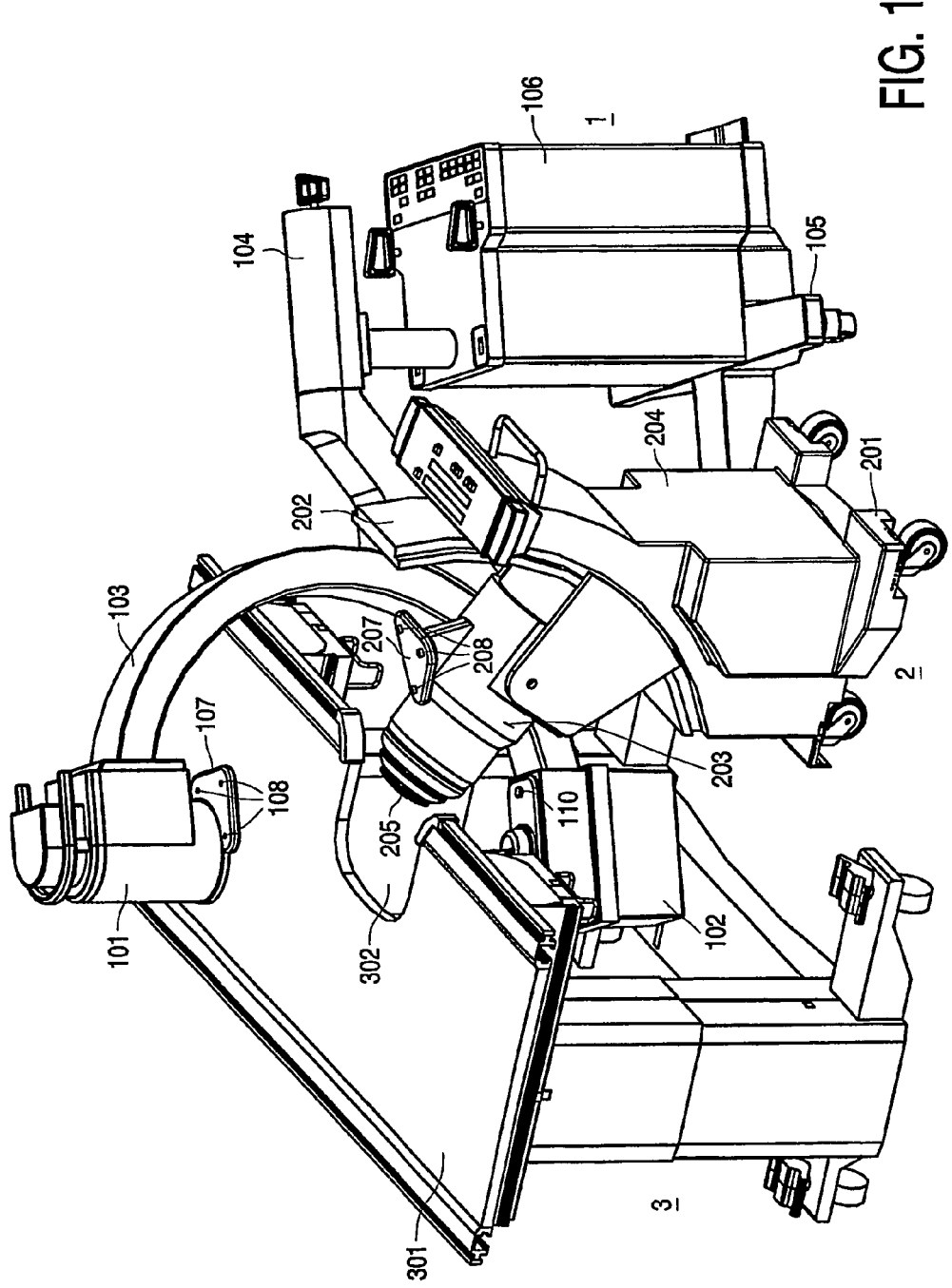

The invention relates to a therapy combination which comprises a therapy unit which is provided with a therapy head for focusing energy in a focus, and also comprises a locating unit for locating a therapy zone within an object, the therapy unit and the locating unit being movable relative to one another.

A therapy combination of this kind is known from U.S. Pat. No. 5,836,898. The therapy combination disclosed therein is formed by a locating unit in the form of an X-ray system with a C-arm mounted on a first carriage and a therapy unit in the form of a lithotripter mounted on a second carriage. The separation of the two units offers the advantage that they can both be used independently of one another.

However, there is the drawback that it is necessary to align the two units relative to one another when a concrement recognized in the X-ray image has to be crushed by the lithotripter. Therefore, the two units can be mechanically coupled to one another in a defined position relative to one another, the focus of the lithotripter then being situated at the point of intersection of the central ray of the X-ray system and a horizontal axis about which the C-arm of the X-ray system can be pivoted. In order to enable coupling in this manner, the constructions of the two units must be adapted to one another and it is not possible, for example, to use a different C-arm X-ray apparatus.

It is an object of the present invention to construct a therapy combination of the kind set forth in such a manner that the two units can co-operate in a simple manner. This object is achieved in accordance with the invention by means of a therapy combination which comprises a locating unit for locating a therapy zone within an object and also comprises a therapy unit which is provided with a therapy head for focusing energy in a focus, the therapy unit and the locating unit being movable relative to one another, there also being provided a measuring device which comprises two sub-systems and serves to determine the relative position of the two sub-systems, one sub-system being attached to the locating unit while the other sub-system is attached to the therapy unit in a defined position relative to the therapy head.

In accordance with the invention the position of the two sub-systems of the measuring device relative to one another is very accurately determined. Because the two sub-systems are rigidly connected to the two units, the position of the focus relative to the locating unit, or the alignment of the locating unit relative to the focus, is also fixed. However, the focus can then be moved to a given position of the therapy zone within an object. In accordance with the invention the constructions of the two units need not be adapted to one another. Therefore, different units can also be modified in accordance with the invention at a later stage.

It is to be noted that U.S. Pat. Nos. 5,944,663 and 5,368,032 already disclose a therapy combination which comprises a measuring device for determining the position in space of the therapy head. One sub-system is formed by (at least) one camera which is arranged in a fixed position in the treatment room while the other sub-system is formed by light-emitting diodes which are attached to the therapy head. Because the locating unit (an MR apparatus or a CT apparatus) is stationary and its position in space is accurately known, the therapy head can thus also be moved to a given position relative to the locating system or its position relative to the locating system can be determined.

Therapy combinations of this kind, however, have the drawback that the relative position is not determined directly but is derived from the position in space of the therapy head. In order to ensure perfect measurement, the lines of sight between the light-emitting diodes and the camera which is mounted in a fixed position in space may not be interrupted, for example, by the staff carrying out the treatment.

This requirement would be very difficult to satisfy if the locating unit were not stationary either and if its position would also have to be determined by means of the camera (or additional cameras). However, when the therapy combination in accordance with the invention is used, the locating unit and the therapy unit are situated very close to one another so that it is rather unlikely that the measurement of the relative position will be influenced by the attendant staff. It is a further advantage that the distance between the two systems in accordance with the invention is comparatively small. Therefore, the absolute measuring error will also be comparatively small.

The relative position determined for the two sub-systems (or for the focus and the locating unit) suffices in principle to move the two units relative to one another to an exactly defined position and to position the object relative to the focus also in such a manner that the zone to be treated is situated in the focus. The user would not have to know this relative position if this alignment or positioning were to take place automatically by means of an appropriate drive. However, this would be a very intricate operation. Therefore, claim 2 discloses a solution which is far simpler. The visualization of the position of the focus in an image as disclosed therein allows the attendant staff to align the two units relative to one another and to position the object to be treated. The position of the focus can then be marked already before an image has been formed by means of the locating unit, because the position of this image is predetermined on the display unit (for example, a monitor), so that from the representation of the mark on the monitor it is already evident where it is situated, for example, relative to the center of the image.

Claim 3 discloses a preferred embodiment of the measuring device. The position and the alignment of the two sub-systems relative to one another can be determined exactly from the times of flight of the ultrasound signals from each of the (at least) three ultrasound transmitters to each of the (at least) three ultrasound receivers when the ultrasound speed is known.

An optical measuring device, in which one or more cameras would have to be attached to one unit and, for example, light-emitting diodes would have to be attached to the other unit, could also be used instead of a measuring device based on ultrasound. In that case a transmission system (light-emitting diodes) would be provided on one unit while a receiving system (camera) would be provided on the other unit. Transmitter and receiver, however, could also be attached to one unit if the other unit were provided with reflecting structures.

Claim 4 discloses a preferred embodiment of the invention. It enables the use of the two units and the room in which they are present for other purposes. However, it is not necessary to mount each of the two units on a respective carriage; one of the two units may also be installed in a fixed position.

Instead of the embodiment disclosed in claim 5, use could also be made of a locating system in the form of an ultrasound imaging system; however, a locating system based on X-rays offers the advantage, for example, when used for lithotripsy, that practically all concrements are reproduced in an X-ray image, whereas many concrements will not become visible in an ultrasound image.

The embodiment disclosed in claim 6 enables simple variation of the radiation direction by means of the C-arm, for example, for three-dimensional localization of a concrement. The further embodiment disclosed in claim 7 then enables measurement of a change of the position of the X-ray converter relative to the X-ray source (for example, due to deformation of the C-arm) by means of a third system so as to take this change into account for the determination of the relative position of the locating unit and the therapy head.

Claim 8 describes the use of a measuring device in a therapy combination as claimed in claim 1.

Claim 9 describes a preferred embodiment of a therapy system provided with a therapy combination in accordance with the invention and with a patient table. Granted, it would also be possible to use a table with a stationary table top, but in that case the therapy head would have to be displaced accordingly and the locating unit would have to follow this displacement at least partly.

Figure 2:
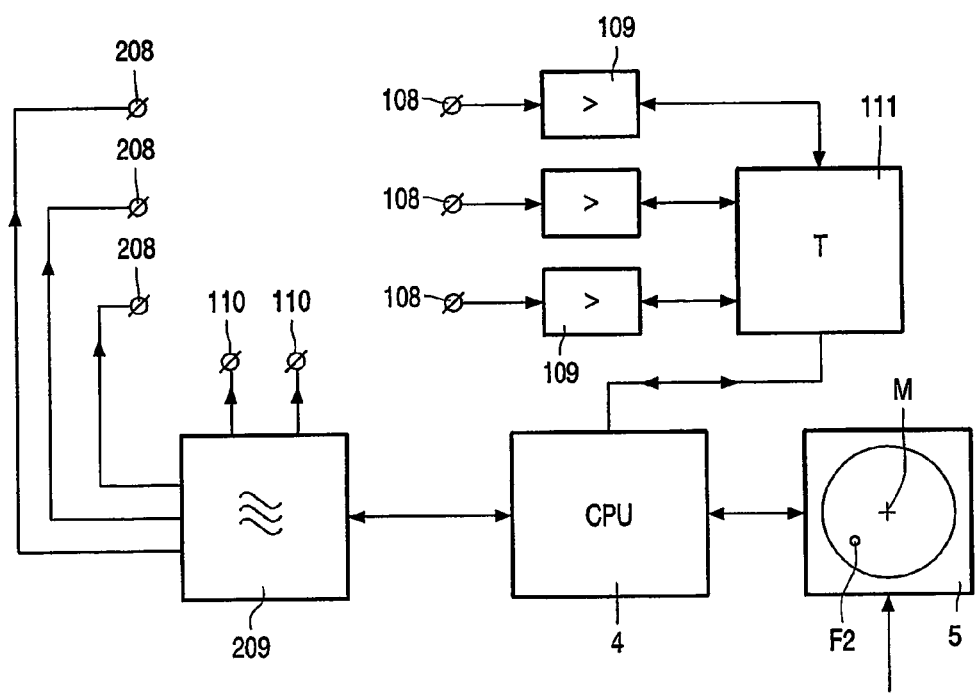

The invention will be described in detail hereinafter on the basis of an embodiment as shown in the drawings. Therein:

FIG. 1 is a perspective view of a therapy system with the therapy combination in accordance with the invention, and FIG. 2 is a block diagram of a part of such a therapy combination.

The reference numeral 1 in FIG. 1 designates a locating unit while the reference numeral 2 designates a therapy unit and the reference numeral 3 designates a patient table.

The locating unit 1 is intended to determine the therapy zone to be treated within a patient who is arranged on the patient table 3 and to position this zone in such a manner that it is situated in the focus of a therapy head of the therapy unit. The locating unit includes an X-ray image converter 101 and an X-ray source 102 which are attached to the ends of a C-arm 103 and are aligned relative to one another. The C-arm 103, and hence the X-ray image converter 101 and the X-ray source 102, can be pivoted in the plane defined thereby and is journaled so as to be pivotable on a horizontal supporting arm 104. The supporting arm 104 is mounted on a carriage 105 so that its height is adjustable; this carriage also accommodates, arranged in a housing 106, the sub-systems required for the power supply of the components 101 and 102 and for the processing of the image signals delivered by the image converter.

Instead of an X-ray locating unit, an ultrasound imaging system could also be used in principle. For lithotripsy applications, however, an X-ray system offers the advantage that it is capable of imaging concrements of practically any type, whereas an ultrasound locating system cannot image given types of concrements. For lithotripsy purposes, therefore, ultrasound locating systems are normally used only as additional systems.

The therapy unit 2 includes a carriage 201 which supports a therapy head 203 which is displaceable and pivotable on an arc-like segment 202. The therapy head 203 serves to generate shockwaves, notably for the crushing of concrements (for example, renal calculi) and may include in known manner a rotation ellipsoid in which an electric discharge takes place via a spark gap, which discharge is fed by a generator 204 which is preferably also arranged on the carriage 201 of the therapy unit 2. The rotation ellipsoid (not shown) communicates with a liquid reservoir (not shown either) which contains a suitable liquid acoustic medium, for example, water, and is sealed from the environment by means of a flexible coupling diaphragm 205. The energy of the shock wave generated is concentrated in one point (the focus) by the rotation ellipsoid, the position of said point relative to the shock wave head 205 being known.

The patient table 3 comprises a table top 301 which serves to accommodate a patient and is displaceable in a horizontal plane. The table top 301, moreover, can be adjusted in respect of height by means of a motor, thus enabling movement of the table top in three mutually perpendicular directions. The table top is provided with a cut-out 302 wherethrough the therapy head 203 can act on a patient arranged on the table top.

In order to enable alignment of the focus of the therapy head 203 relative to the therapy zone in the form of a concrement inside the patient, the concrement must be located by means of the locating unit 1, that is, by way of an X-ray exposure or X-ray fluoroscopy, and its position in the X-ray image must be related to the position of the focus of the therapy head. To this end, there is provided a measuring device whereby the relative position is determined of the locating unit 1 and the therapy unit 2. The measuring device includes two sub-systems, one of which is rigidly connected to the X-ray image converter 101 whereas the other sub-system is rigidly connected to the therapy head 203.

The sub-system connected to the X-ray image converter 101 includes a plate 107 on which (at least) three ultrasound microphones 108 are arranged in such a manner that they define a triangle (that is, not a line). The sub-system connected to the therapy head 203 includes a plate 207 on which (at least) three ultrasound transmitters 208 are arranged in such a manner that they too do not define a line but a polygon (triangle).

FIG. 2 is a block diagram of the measuring device and some further components of the therapy combination. The ultrasound transmitters 208 are connected to a generator 209 which is controlled by an arithmetic and control unit 4 in such a manner that the three ultrasound transmitters successively transmit pulse-shaped ultrasound signals. The ultrasound signals are received by the three ultrasound receivers 108, are amplified by amplifiers 109 and applied to an evaluation unit 111 which, together with the generator 209, forms part of an ultrasound measuring device which measures the times of flight of the ultrasound signal from the respective active ultrasound transmitter to each of the three ultrasound receivers and stores these times, if desired.

When the ultrasound speed is known, the distances between the active ultrasound transmitter and each of the three receivers can be calculated from the times of flight measured (by means of the arithmetic and control unit 4). The position of the active transmitter relative to the three receivers is thus defined. For the positions of the other two ultrasound transmitters, however, various possibilities still exist and the relation in space between the two sub-systems 107, 108 and 207, 208 is unambiguously defined only after the times of flight from all ultrasound transmitters to all ultrasound receivers have been measured and the corresponding distances have been calculated therefrom. This also defines the position and the orientation of the X-ray system 101, 102 in relation to the therapy head 203 or, because of the known position of the focus relative to the therapy head, in relation to the focus.

The execution of a treatment by means of the therapy system shown in FIG. 1 will now be described in detail.

First the patient to be treated is arranged on the table top 3 in such a manner that the zone in which the concrement is expected to be present is situated at the area of the cut-out 302. The therapy unit 2 is then moved towards the patient until the diaphragm 205 of the therapy head 203 contacts the patient. Subsequently, the locating system 1 is moved closer;

the X-ray source 102 and the image converter 101 should then be aligned relative to one another in such a manner that a vertical central ray is obtained (being the connecting line between the focal spot of the X-ray source 102 and the center of the image converter 101). Subsequently, the relative position of the two units 1 and 2 is determined and hence the position of the focus relative to the central ray. The position of the focus as calculated by the arithmetic and control unit 4 is reproduced by way of a mark $F_2$ on a monitor 5 on which subsequently the X-ray image is also displayed. The position of the central ray is defined by the center M of the image which is fixed already before the formation of the X-ray image. The mark $F_2$ for the focus is then displayed in the position in the image in which the focus would appear in an X-ray image if it were to consist of a material-absorbing X-rays and if it were projected onto the image converter 101 by X-rays.

The carriage 105 of the locating unit 1 is then displaced until the mark $F_2$ coincides with the center M of the image, that is, until the focus is situated on the (vertical) central ray.

Subsequently, an X-ray image is formed by means of an X-ray exposure or by X-ray fluoroscopy, said image being displayed on the monitor M. The therapist then defines in this first X-ray image, for example, by means of cross-hairs which can be moved by way of a suitable input unit, the position of the concrement to be crushed, said position usually not being coincident with the center M. Subsequently, controlled either manually or automatically by the position of the cross-hairs in relation to the center M of the image, the patient table 301 is displaced horizontally until the concrement appears at the same point of the X-ray image as the focus. Generally speaking, the focus and the concrement still do not coincide in space in all cases. However, they are situated on the central ray, that is, one over the other in the vertical direction.

Subsequently, the X-rays are switched off and the C-arm 103 is pivoted in such a manner that the central ray extends, for example, at a defined angle of, for example, 30° relative to the vertical. The position of the focus is determined again and the mark $F_2$ is reproduced in this image. It will usually no longer be situated at the center of the image. Generally speaking, the concrement will usually no longer be imaged at the center M either in the X-ray image formed again in this position of the C-arm. However, because the focus and the concrement have already been positioned on a vertical line, it is now only necessary to lift or lower the table top 301 until the focus and the concrement coincide in this image. Subsequently, shock waves for crushing the concrement can be generated by means of the therapy head, the concrement then being situated exactly in the focus.

In practice the C-arm is not rigid, but may become deformed under the influence of the weight of the components 101 and 102 (and its own weight). This deformation can be determined by means of a monitoring device, comprising a finther ultrasound transmitter 110 (only one is shown in FIG. 1), by measuring also the times of flight from these ultrasound transmitters to the ultrasound receivers 108 in each of the two irradiation directions, by determining therefrom the position and the alignment of the two components 101 and 102, and by calculating therefrom the deformation that can then be used to correct the positioning.

An advantage of the invention resides in the fact that the constructions of the locating unit 1 and the therapy unit need not be adapted to one another, as opposed to, for example, the therapy combination mentioned in the preamble. This makes it possible to modify already existing units in the sense of the invention. In that case usually a (one time) calibration measurement is necessary to determine, using suitable phantom bodies, the position and the orientation of the central ray in relation to the sub-system 107, 108 of the measuring device, connected to the locating unit 1, and also the position of the focus in relation to the sub-system 207, 208 which is connected to the therapy head 203.

The therapy head can also generate the shockwaves in a manner other than by means of a discharge of a spark gap. The therapy head may also be active in a manner other than by means of shockwaves, for example, as described in the previously cited U.S. Pat. Nos. 5,944,663 and 5,368,032.

The invention claimed is:

1. A therapy combination comprising:
a locating unit for locating a therapy zone within an object;
a therapy unit which is provided with a therapy head for focusing energy in a focus, the therapy unit and the locating unit being movable relative to one another; and
a measuring device which comprises two sub-systems and serves to determine the relative position of the two sub-systems, one sub-system being attached to the locating unit while the other sub-system is attached to the therapy unit in a defined position relative to the therapy head, wherein the locating unit enables an alignment of the focus of the therapy head relative to a central ray in the therapy zone in response to a determination of the relative position and orientation of the two-subsystems with respect to one another, wherein the sub-system attached to the locating unit includes at least three receivers arranged in a manner that defines a triangle. and wherein the other sub-system attached to the therapy unit includes at least three transmitters arranged in a manner that defines a polygon, the at least three transmitters configured to successively transmit pulse-shaped signals, wherein the sub-system attached to the locating unit is configured to receive the successively transmitted signals from an active one of the at least three transmitters and measure the times of flight of the signals from a respective active transmitter to each of the at least three receivers, the sub-system attached to the locating unit further for measuring times of flight from all transmitters to all receivers.

2. A therapy combination as claimed in claim 1, which comprises a display unit for the display of images formed by means of the locating unit, and also comprises means for determining the position of the focus in an image formed by the locating unit from the determined relative position of the sub-systems, and also means for generating a mark characterizing the position in the image.

3. A therapy combination as claimed in claim 1, in which one sub-system comprises an ultrasound transmission unit with at least three ultrasound transmitters which are situated at a distance from one another whereas the other sub-system includes an ultrasound receiving unit with at least three ultrasound receivers which are situated at a distance from one another, there being provided means for measuring the times of flight of the ultrasound signals from the ultrasound transmitters to the ultrasound receivers and means for determining the position of the ultrasound receiving unit relative to the ultrasound transmission unit.

4. A therapy combination as claimed in claim 1, in which the therapy unit and the locating unit are displaceable on a respective carriage.

5. A therapy combination as claimed in claim 1, which comprises a locating system provided with an X-ray source and an X-ray image converter.

6. A therapy combination as claimed in claim 5, in which the X-ray source and the X-ray image converter are attached to the ends of a C-arm, the associated sub-system of the measuring device being attached to the C-arm or to one of the components attached thereto, preferably to the X-ray image converter.

7. A therapy combination as claimed in claim 6, in which the sub-system associated with the locating unit is attached to the X-ray image converter or to the X-ray source, and a third sub-system which co-operates therewith is attached to the X-ray source, or to the X-ray image converter, in order to monitor the relative position of the X-ray image converter and the X-ray source.

8. The use of a measuring device with two sub-systems-which are to be attached to the units of a therapy combination as claimed in claim 1 in order to determine the relative position of the two sub-systems or of the units.

9. A therapy system which comprises a therapy combination as claimed in claim 1 and a patient table whose table top can be displaced in three mutually perpendicular directions.

* * * * *